United States Patent
Harris, Jr. et al.

(10) Patent No.: US 7,084,096 B2
(45) Date of Patent: *Aug. 1, 2006

(54) SUSPENSION OF BORATES IN NON-AQUEOUS SOLVENTS AND USE THEREOF

(75) Inventors: William Franklin Harris, Jr., Ponca City, OK (US); David Nigel Harry, Sugarland, TX (US); Xiaoping Qiu, Sugarland, TX (US)

(73) Assignee: Benchmark Research & Technology, LLC, Houston, TX (US)

(*) Notice: Subject to any disclaimer, the term of this patent is extended or adjusted under 35 U.S.C. 154(b) by 344 days.

This patent is subject to a terminal disclaimer.

(21) Appl. No.: 10/441,500

(22) Filed: May 20, 2003

(65) Prior Publication Data

US 2003/0220203 A1    Nov. 27, 2003

Related U.S. Application Data

(63) Continuation-in-part of application No. 09/905,358, filed on Jul. 13, 2001, now Pat. No. 6,743,756.

(51) Int. Cl.
*C09K 8/68*  (2006.01)
*C09K 8/62*  (2006.01)
*E21B 43/26* (2006.01)

(52) U.S. Cl. ............. 507/273; 507/261; 507/265; 507/211; 507/216; 507/224; 507/903; 507/922; 166/308.3

(58) Field of Classification Search ........... 507/273, 507/261, 265, 211, 216, 224, 903, 922; 166/308.3
See application file for complete search history.

(56) References Cited

U.S. PATENT DOCUMENTS

| | | | |
|---|---|---|---|
| 3,058,909 A | 10/1962 | Irving et al. |
| 3,629,398 A | 12/1971 | Schmidtt |
| 3,670,065 A | 6/1972 | Eriksson et al. |
| 3,780,170 A | 12/1973 | Goodhart et al. |
| 3,974,077 A | 8/1976 | Free |
| 4,620,596 A | 11/1986 | Mondshine |
| 4,673,526 A | 6/1987 | Zabotto et al. |
| 5,082,579 A | 1/1992 | Dawson |
| 5,091,448 A | 2/1992 | Hostettler et al. |
| 5,145,590 A | 9/1992 | Dawson |
| 5,160,643 A | 11/1992 | Dawson |
| 5,169,552 A | 12/1992 | Wise |
| 5,205,953 A | 4/1993 | Dixit |
| 5,279,755 A | 1/1994 | Choy et al. |
| 5,304,376 A | 4/1994 | Friedrichs et al. |
| 5,311,946 A | 5/1994 | Harry et al. |
| 5,466,846 A | 11/1995 | Sharif |
| 5,468,418 A | 11/1995 | Rabone |
| 5,488,083 A | 1/1996 | Kinsey, III et al. |

(Continued)

OTHER PUBLICATIONS

James A. Kent, Ph.D., Riegel's Handbook of Industrial Chemistry, Animal and Vegetable Fats Oils, and Waxes, 9th Ed., 273-314.

*Primary Examiner*—Philip C. Tucker
(74) *Attorney, Agent, or Firm*—Jenkens & Gilchrist, a Professional Corporation (57) ABSTRACT

A non-aqueous suspension including boron-containing particulates, a low molecular weight polyalkylene glycol and a suspension stabilizer is provided. Methods of crosslinking water soluble polymers and of fracturing a subterranean formation are also provided.

71 Claims, 1 Drawing Sheet

U.S. PATENT DOCUMENTS

| | | |
|---|---|---|
| 5,565,513 A | 10/1996 | Kinsey, III et al. |
| 5,628,990 A * | 5/1997 | Murphy et al. ............... 424/65 |
| 5,631,313 A | 5/1997 | Bishop et al. |
| 5,648,421 A | 7/1997 | Thiele et al. |
| 5,707,551 A | 1/1998 | Pallas et al. |
| 5,834,533 A | 11/1998 | Patel et al. |
| 5,879,705 A | 3/1999 | Heafield et al. |
| 5,906,962 A | 5/1999 | Pallas et al. |
| 5,925,182 A | 7/1999 | Patel et al. |
| 5,969,012 A | 10/1999 | Harris, Jr. |
| 5,985,801 A | 11/1999 | Hoff |
| 6,171,386 B1 | 1/2001 | Sabins |
| 6,225,264 B1 | 5/2001 | Moorhouse et al. |
| 6,251,838 B1 | 6/2001 | Moorhouse et al. |
| 6,361,783 B1 * | 3/2002 | Moaddel et al. ............ 424/401 |
| 6,743,756 B1 * | 6/2004 | Harris, Jr. ................... 507/261 |
| 2002/0182157 A1 * | 12/2002 | Grayson ...................... 424/64 |
| 2004/0010066 A1 * | 1/2004 | Devine ....................... 524/409 |

* cited by examiner

SUSPENSION OF BORATES IN NON-AQUEOUS SOLVENTS AND USE THEREOF

CROSS REFERENCE TO RELATED APPLICATIONS

This application is a continuation-in-part of U.S. application Ser. No. 09/905,358 which was filed on Jul. 13, 2001, now U.S. Pat. No. 6,743,756.

FEDERALLY SPONSORED RESEARCH

Not applicable.

REFERENCE TO MICROFICHE APPENDIX

Not applicable.

FIELD OF THE INVENTION

The present invention relates to stable, concentrated, non-aqueous suspensions of boron-containing particulates, such as suspensions of boric acid and/or the alkaline metal borates (hereinafter collectively referred to as "boron suspensions" or "boron crosslinkers") with excellent storage stability. More specifically, a low molecular weight polyalkylene glycol is used as the suspension medium, and a hydrogenated castor wax or oil is used to stabilize the suspension. The present invention further relates to methods of using such suspensions.

BACKGROUND OF THE INVENTION

When gas and/or oil is removed from a subterranean formation through drilling, the pressure in the formation declines. As a result of the pressure decline, the production of oil and/or gas from the well also declines. Although oil and/or gas may still be present in the formation, production may decrease to such an extent that further removal of oil and/or gas becomes uneconomical. This is particularly true where the cost of producing the oil and/or gas from the formation is very high, such as it is in offshore production operations. In such cases, it is crucial to extract as much oil and/or gas from the formation as possible. Production from formations in which the pressure has declined may be raised by techniques generally known as well stimulation. To stimulate an oil and/or gas well, a fracturing fluid is injected into the formation, under high pressure, via the well's bore hole. By applying hydraulic pressure within the formation, the fracturing fluid fractures the subterranean strata surrounding the bore hole, thereby increasing and extending the area from which oil and/or gas may be drained.

The most efficient hydraulic fracturing of a subterranean formation ideally requires that the fracturing fluid reach its maximum viscosity just as it enters the fracture. Increasing the viscosity of the fracturing fluid, which improves its ability to fracture the formation rock, is usually accomplished by crosslinking a water-soluble polymer (such as guar, hydroxypropyl guar, carboxymethyl guar, or carboxymethyl hydroxypropyl guar) solution. The crosslinkers used for this purpose are typically selected from the group of elements comprising aluminum, boron, and the transition metals. Currently, boron and zirconium are the elements most preferred for crosslinking aqueous solutions of water-soluble polymers.

A number of boron compounds have historically been used to crosslink the polymers employed in fracturing fluids, but there are a number of disadvantages inherent in the use of each of the currently available boron crosslinkers; including, for example, (1) some are limited to use only in low temperature (e.g., less than about 200° F. bottom-hole static temperature) applications: (2) some are difficult to control with respect to their crosslinking reaction rate, (3) some possess constituents (such as the divalent hardness ions) that are incompatible with optimum fracturing fluid performance; (4) some have poor "shelf life" and/or present other handling difficulties during well treatment; (5) some are typically very dilute (in some cases with boron concentrations a mere 10% of those of the boron crosslinker of the present invention); (6) some present environmental, health, and/or safety concerns (such as those that contain methanol or diesel as a diluent, and as such are toxic, flammable, or both); and (7) some are extremely costly and difficult to manufacture.

In addition, certain boron-containing aqueous solutions used in crosslinking systems are made at the job site by mixing solid boron-containing compounds with water or another aqueous fluid. A number of disadvantages are inherent in job-site mixing procedures, particularly when well treatment requires that large volumes of solutions be prepared. For example, special mixing equipment for mixing the solids with water is required, and extended preparation and mixing time are involved. In addition, the mixing and physical handling of large quantities of dry chemicals require a great deal of manpower, and where continuous mixing is required, the accurate and efficient handling of chemicals is extremely difficult. Thus, the use of job-site prepared aqueous boron-containing crosslinkers drives up labor costs. Moreover, uneven mixing and the low solubility of the boron solids may allow or even cause lumps to form in the crosslinker fluid, which lowers the effective concentration of the cross-linker. The time and labor necessary to assure complete solubilization and dispersion of the boron compounds used in job-site prepared crosslinkers not only further drives up costs, but also increases the likelihood that the fracturing fluid will perform poorly, or not at all.

The job-site preparation of aqueous boron-containing solutions from solids also generates fugitive dust, and the presence of such dust creates the potential for its inhalation by workers preparing the solution. The dust may produce a respiratory allergenic response and/or irritation in some individuals. Fugitive dust also raises environmental concerns.

The problems associated with mixing solids at the job site present such substantial concerns as to effectively prevent many offshore operators from using such systems. Nonetheless, because boron crosslinkers are so effective in raising the viscosity of water-soluble polymer-based fracturing fluids, there remains a desire and a need to use such crosslinkers.

In an effort to take advantage of the efficiency of boron crosslinkers while avoiding the cost, safety and environmental problems associated with their job site preparation, liquid slurries or suspensions of boron-containing solids have been used. Such suspensions are then added to the aqueous polymer systems. A number of methods for accomplishing this, and the compositions prepared thereby, are described in the prior art. However, such methods present significant disadvantages. Specifically, known slurry and suspension methods use oil carriers (e.g., mineral, isoparaffin or diesel, or hydrocarbon solvents, such as mineral spirits) to suspend and deliver the boron compounds to the aqueous systems.

Examples of suspension systems utilizing mineral spirits are disclosed in U.S. Pat. Nos. 5,488,083 and 5,565,513. Recent regulations promulgated by the Environmental Protection Agency, however, limit the amount of oil or grease that can be used in well treatment fluids for offshore oilfield applications. Current regulations limit the oil and grease to a daily maximum concentration of 42 mg/l and a monthly average of 29 mg/l when the suspension is diluted to the intended use level with fresh or salt water The suspension of the present invention has hexane extractable oil and grease of less than about 30 ppm. Many of the currently available slurry and suspension systems, upon being diluted to the concentrations intended for use in fresh or salt water for a well treatment fluid, contain a much higher concentration of oil and/or grease than is permitted by the current Regulations. Thus, many of the available slurry and suspension systems are useless in offshore operations. Moreover, regulatory limits are likely to decrease, rather than increase, in the future. It is also well known that many of the oil carriers have a Pensky Martens closed cup flash point of about 140° F. or less, and as such may be classified as combustible. Pensky Martens closed cup flash point method ("PMCC") is discussed in 29 CFR 1910.1450 and further provides a definition for "combustible liquid" as "any liquid having a flashpoint at or above 100° F. (37.8° C.), but below 200° F. (93.3° C.), except any mixture having components with flashpoints of 200° F. (93.3° C.), or higher, the total volume of which make up 99% or more of the total volume of the mixture." Moreover, 29 CFR 1910.1450 defines a flash point as "the minimum temperature at which a liquid gives off a vapor in sufficient concentration to ignite when tested as follows: . . . (ii) Pensky Martens Closed Tester (see American National Standard Method of Test for Flash Point by Pensky Martens Closed Tester, Z117.1979 (ASTM D9379)) for liquids with a viscosity equal to or greater than 45 SUS at 100° F. (37.8° C.), or that contain suspended solids, or that have a tendency to form a surface film under test."

In addition to the foregoing, because of the relatively low solubility of boron compounds in water, aqueous boron solutions used as crosslinkers may comprise a significant percentage (up to about 10%) of the total crosslinked fluid volume. The need for such high crosslinker volumes increases treatment costs by requiring additional equipment to transport and hold the crosslinker at the well-site. Further, such comparatively high volumes for the crosslinker additive potentially increases production costs by increasing the quantity of spent-fracturing fluid that must be recovered after the well is treated and before it can be made to produce oil or gas.

As discussed above, the currently available boron crosslinking systems present cost, health, safety, and/or environmental concerns. However, production unreliability is also a major drawback of the current systems. For example, the systems disclosed in U.S. Pat. Nos. 5,488,083 and 5,565,513 are extremely water sensitive, in that the crosslinker forms a granular precipitate or sludge in the presence of small amounts of water. This makes the crosslinker difficult-to-impossible to handle in the field, due to the potential for contamination from pumps or lines that have had water in them. While such systems have limited viability in land-based operations, they are virtually useless for offshore applications.

In addition to the environmental and water-compatibility concerns, known crosslinker suspension or slurry systems are not sufficiently stable for long term storage. That is, the boron-containing particles separate from the suspensions and settle in as little as about two to four weeks. In such time periods, the settled particles form a hard pack which either cannot be re-suspended or can only be re-suspended with extensive mixing. The inability to store such suspensions for periods longer than about two weeks presents scheduling and/or waste problems, particularly in difficult-to-reach areas, such as offshore drilling platforms.

Yet another treatment concern in using any of the currently available boron-containing crosslinking systems is the possibility of premature gelation while the fracturing fluid is in the bore hole. Premature gelation can result in poor performance, thereby further increasing treatment costs. Numerous systems that delay gelation have been developed to address the problem of premature gelation, but such delayed boron crosslinkers may be too effective for use in cold-water and/or cold-treatment applications, where the onset of crosslinking may occur substantially later than desired, i.e., after the fracturing fluid has entered the formation.

For example, extended delay times are a particular problem in applications where the fracturing fluid make-up water is colder than about 50° F., such as during the winter and in offshore treatment operations. In such circumstances, the crosslink delay time will become much longer than the well treatment will tolerate. Therefore, a need also exists for accelerated crosslinking when (1) there is a need to use cold field make-up water during cold seasons or in cold climates, (2) the wells to be treated are shallow, or (3) the fracturing fluid is required to crosslink in cold well bores, such as those commonly encountered in offshore operations.

As the availability of onshore oil supplies, particularly those located in the Middle East, becomes increasingly unsure, the ability to maximize domestic production from offshore and remote, cold region production operations will become increasingly critical to a continuous oil and gas supply. There therefore exists a need for a boron-containing crosslinking suspension system which meets the current regulatory limits for oil and grease concentrations, which is stable for long periods of time, and in which the crosslinking reaction rate may be readily accelerated in cold conditions. The present invention is directed to satisfying these needs and to overcoming the problems encountered with the boron crosslinker suspensions currently available, as discussed above.

SUMMARY OF THE INVENTION

The present invention overcomes the problems discussed above by providing a non-aqueous suspension, a boron crosslinker suspension, a method for crosslinking water soluble polymers, a method for controlling the crosslinking reaction rate, and a method of fracturing a subterranean formation.

In accordance with one aspect of the present invention, boron-containing particulates are held in a non-aqueous suspension containing a low molecular weight polyalkylene glycol and a suspension stabilizer. Such a suspension is extremely stable, with little or no particulate settling, and no hard packing of the particulates for time periods of at least one month.

In accordance with another aspect of the present invention, non-aqueous boron crosslinker suspensions for crosslinking fracturing fluids are provided. The crosslinker suspensions are extremely stable for time periods of at least one month and contain no extractable grease or oil.

In accordance with yet another aspect of the present invention, a method of fracturing a subterranean formation by accelerating the crosslinking reaction rate is provided where the method is effective in cold environments, such as those encountered in cold climates or in offshore fracturing treatments.

DESCRIPTION OF EMBODIMENTS OF THE INVENTION

The objectives of the present invention are accomplished by the formulation of a three component polyalkylene glycol based boron particulate suspension system. It has been found that when a small amount of a hydrogenated castor oil or wax is added to a polyalkylene glycol-based suspension, the resulting suspension is extremely stable for periods of time of at least one month and can be caused to accelerate the crosslinking of a water-soluble polymer based fracturing fluid readily and quickly with the addition of water. Moreover, the crosslinker suspension of the present invention is found to have no extractable grease or oil using methods prescribed by current environmental regulations.

The first component of the boron crosslinker suspension system of the present invention is a boron compound. Boron compounds suitable for suspension in the present invention include, but are not limited to, anhydrous alkaline metal borates, hydrated forms of alkaline metal borates, boric acid, or a mixture of any of the foregoing boron compounds. Typically, the boron particles will have an average particle size between about 0.1 micron and about 600 microns. More preferably, the particles will have an average particle size between 1 micron and 300 microns. Most preferably, the particles will have an average particle size between 5 microns and 200 microns. The boron particles may comprise from about 0.1% by weight to about 60% by weight of the total suspension weight. The boron content of the boron suspension may comprise from about 100 ppm (0.01 wt %) boron to about 450,000 ppm (45 wt %) boron.

The second component of the boron crosslinker suspension system of the present invention is polyalkylene glycol or thickened polyalkylene glycol, used as the suspension medium. The suspension medium varies from about 24 wt % to about 99.8 wt % of the total weight of the suspension. Particularly preferred is the use of polyethylene glycol or polypropylene glycol, and mixtures thereof. Most preferred is the use of low molecular weight polyalkylene glycols having a molecular weight of less than 1000; more preferably having a molecular weight between 100 and 600; and most preferably having a molecular weight between 200 and 500.

The term "thickened polyalkylene glycol" refers to polyalkylene glycols having preferably between 0.1% and 4% thickener selected from the group consisting of partially neutralized polyacrylic acid, hydroxypropyl cellulose, highly substituted hydroxypropyl guar, or hydrated thickening silica (including fumed silica and hydrophobic fumed silica). The preferred hydrated thickening silicas, often merely called "thickening silicas," are colloidal gel silicas or hydrophobic derivatives thereof. More preferred ones are Aerosil®200 silica, available from Degussa Corporation, Ridgefield Park N.J., and CAB-O-SIL® M-5 and TS-530 available from Cabot Corporation, Tuscola, Ill. The most preferred is CAB-O-SIL® TS-530.

The third component of the boron crosslinker suspension system of the present invention is a suspension stabilizer, a finely divided hydrogenated castor oil or wax. Most preferably this hydrogenated oil or wax is hydrogenated castor wax. This material is present in the boron crosslinker suspension system of the present invention in amounts from about 0.1% to about 5% by weight; more preferably in the amount of 0.3% to 3% by weight; and most preferably in amounts of 0.5% to 2% by weight of the suspension. The preferred hydrogenated castor waxes are sold by Süd Chemie of Louisville, Ky. under the names of RheocinT® and Rheocin®

In addition to the three components of the boron crosslinker suspension system described above, the suspension of the present invention may also contain one or more additives selected from the group consisting of salts, pH buffers, surfactants, emulsifiers, demulsifiers, foaming agents, antifoaming agents, water miscible co-solvents, clay stabilizers, corrosion inhibitors, scale removers, paraffin solvents, iron chelants, hardness ion chelants, antioxidants, biocidal agents, gel preservatives and gel breakers, antifoaming agents, corrosion inhibitors, preservatives, surfactants, water miscible cosolvents and other materials which might aid the performance of the solid boron particulates in their intended applications.

The boron crosslinker suspension of the present invention is preferably formed by mixing the boron particulate and the hydrogenated castor oil or wax with the polyalkylene glycol, followed by the agitation of this mixture. In the laboratory, this is accomplished by agitating the mixture for a period of from about 30 minutes to about 2 hours; more preferably from about 45 minutes to about 90 minutes; and most preferably from about 55 minutes to about 70 minutes. The mixture agitated for such periods is homogeneous, easily pourable, and possesses a smooth texture. One of ordinary skill in the art of crosslinker suspension preparation would be able to easily adjust mixing and agitation times and conditions to attain a homogeneous, easily pourable and smooth suspension. The resulting suspension may be stored in dry containers for a period of at least one month.

In another aspect of the present invention, a method for crosslinking water soluble polymers is provided. In such method, an effective amount of the boron crosslinker suspension of the present invention—comprising solid boron-containing particulates, polyalkylene glycol (or thickened polyalkylene glycol) and a suspension stabilizer—is added to a hydrated or colloidal dispersion of a water soluble polymer. Boron concentrations in fracturing fluids may vary considerably depending upon many factors, including, among others, the amount of water soluble polymer to be crosslinked, the intended crosslinking rate, the treating temperature of the fracturing fluid, and the pH of the fracturing fluid. Those of ordinary skill in the art of formulating and employing fracturing fluids will be able to adjust the loading of the boron crosslinker of the present invention as required by the treatment application.

The crosslinkable water-soluble polymer may be selected from the group of polyvinyl alcohols, starches, derivatized starches, guar, derivated guars, and locust bean gum. The water soluble polymers most often employed in fracturing applications and useful with the inventive boron crosslinker are guar, hydroxypropyl guar, carboxymethyl guar, and carboxymethyl hydroxypropyl guar.

The boron crosslinker suspension of the present invention further provides a method for fracturing a subterranean formation by forming a hydraulic fracturing fluid which includes the boron crosslinker suspension of the present invention, a water soluble polymer, and water, and by pumping that fracturing fluid under pressure into a subterranean formation. Initial pumping pressures and conditions are well known to those skilled in the art of hydraulic fracturing. The water used in mixing the fracturing fluid may be fresh or saltwater and may be at any liquid temperature. In order for crosslinking to occur (i.e., to be effective as a crosslinker for fracturing applications), the boron crosslinker of the present invention must be employed with fracturing fluids possessing a pH of about 8.5 or greater. Methods of raising the pH of fracturing fluids are well known to those skilled in the art of hydraulic fracturing, and may include pH adjustments before or after the addition of the boron crosslinker of the present invention.

The boron crosslinker suspension of the present invention provides a method for fracturing a subterranean formation by controlling the rate of crosslinking in the formation of a hydraulic fracturing fluid. Because of the inherent properties of boron particulates in suspension, boron crosslinker suspensions typically display a delayed crosslinking reaction rate, compared to that of a completely solubilized boron crosslinker. The crosslinking reaction rate of the boron crosslinker of the present invention can be even further delayed by the addition of alkaline buffers to the water soluble polymer solution. Surprisingly, the crosslinking reaction rate of the boron crosslinker of the present invention can also be accelerated in a controlled manner by the regulated addition of water to the crosslinker suspension.

These and other aspects of the present invention may be seen from the Examples that follow. Example 1 describes the composition and method to manufacture one embodiment of the boron crosslinker suspension system. Comparative Example 2 describes a boron crosslinker suspension which employs no thickener. Comparative Example 3 describes a boron suspension system employing the high oil and grease suspension medium of most currently employed suspended borate crosslinkers. Example 4 describes the composition and method to manufacture another embodiment of the boron crosslinker suspension system in which the boron compound is boric acid. Comparative Example 5 addresses the boron crosslinker suspension of Comparative Example 2, where boric acid is used in lieu of sodium tetraborate, and which employs no thickener. Example 6 illustrates the comparative water sensitivity of boron crosslinker suspension systems prepared according to Example 1 and Comparative Example 3. Example 7 demonstrates the effect of water concentration in the boron suspension system of Example 1 on the crosslinking reaction rate of a water-soluble polymer solution. Comparative Example 8 demonstrates the effect of water concentration in the boron suspension system of Comparative Example 3 on the crosslinking reaction rate of a water-soluble polymer solution. Example 9 demonstrates the effect of water concentration in the boron suspension system of Example 1 on the crosslinking reaction rate of a water-soluble polymer solution where the temperature of the fluid is cooled from room temperature to 40° F.

EXAMPLE 1

810 grams of a powdered anhydrous sodium tetraborate and 20 grams of Rheocin® were dispersed into 1160 grams of polyethylene glycol (200 MW) pre-thickened with 10 grams of thickening silica, specifically CAB-O-SIL® TS-530, in a 2000 ml beaker. The mixture was agitated using an overhead mixer at 700 rpm for a period of 1 hour. The viscosity of the mixture was measured on a Brookfield RV viscometer at 20 rpm using a #4 spindle. A portion of the contents were transferred to a 100 ml graduated cylinder for subsequent measurement of the supernatant separation over time. The balance of the material was transferred to another container for evaluation of particle packing and other properties as desired.

| Composition (% by weight): | |
|---|---|
| Sodium tetraborate | 40.5% |
| Rheocin ® | 1.0% |
| Pre-thickened Polyethylene glycol 200 MW | 58.5% |
| Initial viscosity | 4610 cP |
| Density | 1.365 g/ml |
| Pounds of sodium tetraborate per U.S. Gallon | 4.6 |
| Pounds of extractable oil and grease per U.S. Gallon | 0 |

| Aging | Supernatant Separation | Particle Packing |
|---|---|---|
| 24 hours | 0% by volume | None |
| 3 days | 0% by volume | None |
| 1 month | 1% by volume | None |
| 3 months | 4% by volume | None |

The above composition is easily pourable or pumpable.

COMPARATIVE EXAMPLE 2

810 grams of a powdered anhydrous sodium tetraborate was dispersed into 1170 grams of polyethylene glycol (200 MW) in a 2000 ml beaker. The mixture was agitated using an overhead mixer at 700 rpm for a period of 1 hour. The viscosity of the mixture was measured on a Brookfield RV viscometer at 20 rpm using a #4 spindle. A portion of the contents were transferred to a 100 ml graduated cylinder for subsequent measurement of the supernatant separation over time. The balance of the material was transferred to another container for evaluation of particle packing and other properties as desired.

| Composition (% by weight): | |
|---|---|
| Sodium tetraborate | 40.5% |
| Polyethylene glycol 200 MW | 59.5% |
| Initial viscosity | 1250 cP |
| Density | 1.37 g/ml |
| Pounds of sodium tetraborate per U.S. Gallon | 4.6 |
| Pounds of extractable oil and grease per U.S. Gallon | 0 |

| Aging | Supernatant Separation | Particle Packing |
|---|---|---|
| 24 hours | 12% by volume | Medium packed. Difficult to remix with stirring rod. |
| 3 days | 22% by volume | Hard packed. Cannot remix with stirring rod. |

| Aging | Supernatant Separation | Particle Packing |
|---|---|---|
| 1 week | 30% by volume | Hard packed. Cannot remix with stirring rod. |
| 1 month | 51% by volume | Hard packing, Cannot remix with stirring rod. |

COMPARATIVE EXAMPLE 3

A suspension was prepared by slurrying 620 grams of anhydrous sodium tetraborate with 1350 grams of mineral spirits for five minutes utilizing an overhead mixer at 700 rpm. The anhydrous sodium tetraborate used in this example had a particle size of less than 60 mesh. At the expiration of five minutes, styrene/isoprene copolymer in an amount of 30 grams was gradually added. After the styrene/isoprene copolymer had been added, the resulting product was agitated for 55 minutes utilizing an overhead mixer at 700 rpm.

| Composition (% by weight): | |
|---|---|
| Mineral Spirits | 67.5% |
| Styrene/Isoprene Copolymer | 1.5 |
| Sodium Tetraborate | 31% |
| Initial viscosity | 2816 cP |
| Density | 1.01 g/ml |
| Pounds of Sodium Tetraborate per U.S. Gallon | 2.54 |
| Pounds of extractable oil and grease per U.S. Gallon | 5.53 |

| Aging | Supernatant Separation | Particle Packing |
|---|---|---|
| 24 hours | 1% by volume | None |
| 3 days | 4% by volume | Some soft settling. Can easily be remixed with stirring rod. |
| 1 week | 6% by volume | Some soft packing. Can be remixed with stirring rod. |
| 1 month | 20% by volume | Hard packing, very difficult to remix. |

Note that although this solution remained mixable after one week, the amount of extractable oil and grease exceeds current regulatory limits.

EXAMPLE 4

240 grams of a powdered anhydrous boric acid and 6 grams of Rheocin® were dispersed into 348 grams of polyethylene glycol (200 MW) pre-thickened with 6 grams thickening silica, specifically CAB-O-SIL® TS-530, in a 1000 ml beaker. The mixture was agitated using an overhead mixer at 700 rpm for a period of 1 hour. The viscosity of the mixture was measured on a Brookfield RV viscometer at 20 rpm using a #4 spindle. A portion of the contents were transferred to a 100 ml graduated cylinder for subsequent measurement of the supernatant separation over time. The balance of the material was transferred to another container for evaluation of particle packing and other properties as desired.

| Composition (% by weight) | |
|---|---|
| Boric acid | 40% |
| Rheocin® | 1% |
| Pre-thickened Polyethylene glycol 200 MW | 59% |
| Initial viscosity | 2250 cP |
| Density | 1.24 g/ml |
| Pounds of boric acid per U.S. Gallon | 4.1 |
| Pounds of extractable oil and grease per gallon | 0 |

| Aging | Supernatant Separation | Particle Packing |
|---|---|---|
| 24 hours | 0% by volume | None |
| 7 days | 0% by volume | None |
| 1 month | 1% by volume | None |

The above composition is easily pourable or pumpable.

COMPARATIVE EXAMPLE 5

240 grams of powdered anhydrous boric acid was dispersed into 360 grams of polyethylene glycol (200 MW) in a 1000 ml beaker. The mixture was agitated using an overhead mixer at 700 rpm for a period of 1 hour. The viscosity of the mixture was measured on a Brookfield RV viscometer at 20 rpm using a #4 spindle. A portion of the contents were transferred to a 100 ml graduated cylinder for subsequent measurement of the supernatant separation over time. The balance of the material was transferred to another container for evaluation of particle packing and other properties as desired.

| Composition (% by weight) | |
|---|---|
| Boric Acid | 40% |
| Polyethylene glycol 200 MW | 60% |
| Initial viscosity | 550 cP |
| Density | 1.31 g/ml |
| Pounds per Boric Acid per U.S. Gallon | 4.4 |
| Pounds of extractable oil and grease per U.S. Gallon | 0 |

| Aging | Supernatant separation | Particle packing |
|---|---|---|
| 24 hours | 50% by volume | Hard packed. Cannot remix with stirring rod. |
| 1 week | 54% by volume | Hard packed. Cannot remix with stirring rod. |
| 1 month | 56% by volume | Hard packing, Cannot remix with stirring rod. |

EXAMPLE 6

This example compares the water sensitivity of the solution prepared in accordance with Example 1 with the water sensitivity of the solution prepared in accordance with Comparative Example 3. 200 grams of the solution of Example 1 were added to each of three separate 600 ml griffin beakers, as was 200 grams of the solution of Comparative Example 3. Each beaker was secured under an overhead mixer. A 3 blade agitator was placed in each beaker 1 inch from the bottom of the beaker. The speed was set to 500 rpm. Water (loadings variable by 5%, 10%, or 20% by volume as the case may be for each of the water sensitivity tests) was added to each beaker to bring the solution to the desired concentration. A timer was started and the contents of the beaker were mixed for 5 minutes at 500 rpm. After 5 minutes mixing, the appearance of the mixture was noted to determine if the suspension was uniform. Mixing speed was adjusted to 1000 rpm and mixing was continued for an additional 5 minutes. The results of this testing are given in Table 1.

TABLE 1

Comparative Water-Sensitivities of Boron Crosslinkers

| Suspension prepared according to: | Ex. 1 | Ex. 1 | Ex. 1 | Ex. 3 | Ex. 3 | Ex. 3 |
|---|---|---|---|---|---|---|
| Volume % Water Added | 5 | 10 | 20 | 5 | 10 | 20 |
| Temperature (° C.) after addition of water | 22 | 22 | 22 | 37 | 46 | 61 |
| 2 Hr Viscosity | 5700 | 6800 | 6000 | 2330 | 2050 | 1450 |
| Appearance | Smooth | Smooth | Grainy | Smooth with precipitate | Smooth with precipitate | Almost clear on top with a large amount of precipitate |

EXAMPLE 7

600 grams of a powdered anhydrous sodium tetraborate and 16 grams of Rheocin® were dispersed into 1384 grams of polyethylene glycol (200 MW) pre-thickened with 24 grams of thickening silica, specifically CAB-O-SIL® TS-530, in a 2000 ml beaker. The mixture was agitated using an overhead mixer at 700 rpm for a period of 1 hour. The viscosity of the mixture was measured on a Brookfield RV viscometer at 20 rpm using a #4 spindle. A portion of the contents were transferred to a 100 ml graduated cylinder for subsequent measurement of the supernatant separation over time. The balance of the material was transferred to another container for evaluation of particle packing and other properties as desired.

| Composition (% by weight): | |
|---|---|
| Sodium tetraborate | 30.0% |
| Rheocin ® | 0.8% |
| Pre-thickened Polyethylene glycol 200 MW | 69.2% |
| Initial viscosity | 5504 cP |
| Density | 1.310 g/ml |
| Pounds of sodium tetraborate per U.S. Gallon | 3.35 |
| Pounds of extractable oil and grease per U.S. Gallon | 0 |

Distilled water was premixed into the boron crosslinker suspension prepared according to Example 1 at concentrations ranging from 0% to 25% by volume. To conduct crosslinking tests, a guar solution was prepared by dissolving 30 grams potassium chloride in 1000 ml distilled water, followed by adding 3.6 grams of high viscosity fracturing fluid grade guar powder, such as Benchmark Polymer-3422 which can be obtained from Benchmark Research & Technology, LLC, Midland, Tex. The resulting mixture was agitated in a Waring blender for 30 minutes to allow hydration of the guar polymer. 200 ml of the guar solution was placed in a glass Waring blender jar. The mixing speed was adjusted to form a vortex in the guar solution so that the acorn nut in the bottom of the blender jar was fully exposed, yet not so high as to entrap significant amounts of air in the guar solution. While mixing, 0.2 ml of 25 weight % sodium hydroxide solution was added before the water-diluted boron crosslinker solution prepared according to Example 1 was added. The boron crosslinker of Example 1 was used as a Control, where 0.2 ml of the crosslinker solution was added to 200 ml of the guar solution to effect crosslinking. Where the water concentration of the boron crosslinker of Example 1 was made to exceed any quantity greater than 0%, the volume of boron crosslinker solution prepared according to Example 1 and its water addition were adjusted so that the boron concentration of the resulting crosslinked guar solution was identical to the Control. The crosslinking rate is expressed by three different time recordings: vortex closure related time readings T1 and T2 and hang lip time T3. T1 is defined as the time that has elapsed between the time that the crosslinker is added and the time when the acorn nut in the blender jar just becomes fully covered by fluid. T2 is defined as the time that has elapsed between the time that the crosslinker is added and the time when the top surface of the fluid in the blender jar has just stopped rolling and becomes static. The blender mixing speed setting remained constant throughout this test (although the actual mixing speed may be reduced as the viscosity of the crosslinked fluid increases). After T2 was recorded, the mixing was stopped and the fluid was passed back and forth between two beakers to observe consistency. Hang lip time (T3) is defined as the time that has elapsed between the time that the crosslinker is added and the time when the crosslinked fluid forms a stiff lip that can hang on the edge of the beaker. Those of ordinary skill in the art of evaluating fracturing fluids will quickly recognize the fundamental tenants of evaluating such fluids in the manner described in this Example, although individual testing practices and procedures may vary from those described herein.

COMPARATIVE EXAMPLE 8

Distilled water was premixed into the boron crosslinker suspension prepared according to Comparative Example 3 at concentrations ranging from 0% to 25% by volume. No crosslinking tests were conducted because each of the crosslinkers manufactured in the fashion described here precipitated such a large portion of the suspended boron that meaningful crosslinking tests could not be conducted.

EXAMPLE 9

The guar solution described in Example 7 and the glass blender jar were pre-cooled so that the fluid temperature before adding the boron crosslinker of the present invention was 40° F. The crosslinking rate tests were then conducted using the method described in Example 7, and the results are given in Table 2.

TABLE 2

Acceleration of crosslinking rate in 40° F. base fluid

| Crosslinker System | Suspension of Example 1 with 0% water | Suspension of Example 1 with 22.5% water |
|---|---|---|
| T1 (seconds) | 237 | 32 |
| T2 (seconds) | >300 | 49 |
| Hang lip time T3 (min:sec) | >10:00 | 2:28 |

DISCUSSION OF THE EXAMPLES

Example 1 describes the composition and method to manufacture the boron suspension system of the present invention where the boron compound is sodium tetraborate. As demonstrated, this boron crosslinker suspension exhibits excellent supernatant separation and particulate packing properties to give it a long shelf life when compared to other crosslinker suspensions currently available. Further, the storage performance of the boron crosslinker of the present invention enhances it usefulness as a crosslinker for fracturing applications. More particularly, due to the absence of any environmentally detrimental constituents, the boron crosslinker suspension of the present invention is suitable for use in environmentally sensitive areas.

Comparative Example 2 describes the boron suspension system of Example 1, except that the composition of Example 2 employs no thickener, demonstrating the advantages of the thickened suspension medium of the claimed invention.

Comparative Example 3 describes a typical boron suspension crosslinker currently in use. The crosslinker so described employs the high oil and grease suspension medium that makes them unsuitable for use in environmentally sensitive areas. Additionally, the supernatant separation and particle packing properties of the boron crosslinker suspension of the claimed invention (as shown in Example 1) are shown to be superior to those of the typical boron crosslinker suspension described in this Example.

Example 4 describes the composition and method to manufacture the boron suspension system described in Example 1 where the boron compound used is boric acid rather than the sodium tetraborate of Example 1. The results demonstrate that the use of boric acid in the boron crosslinker suspension of the claimed invention provide the same advantages as those found in the boron crosslinker suspension which uses sodium tetraborate.

Comparative Example 5 describes the composition and method to manufacture the boron crosslinker suspension of Comparative Example 2 where (1) the boron compound used is boric acid rather than sodium tetraborate, and (2) the polyethylene glycol is not pre-thickened. The boron crosslinker of this Comparative Example 5 exhibits supernatant separation and particle packing properties which are inferior not only to those of the sodium tetraborate and boric acid crosslinker compositions described in Examples 1 and 4, respectively, but also to those of the typical boric acid crosslinker composition described in Comparative Example 3.

Example 6 illustrates the comparative water sensitivity of boron crosslinker suspension systems prepared according to Example 1 and Comparative Example 3; Example 1 represents the claimed invention, whereas Comparative Example 3 represents the typical boron suspension currently in use. Table 1 contains the results of a comparison to the water tolerance of these two crosslinker examples. It can be clearly seen from the data given that the boron crosslinker of the claimed invention has superior water tolerance to the typical boron crosslinker suspension now in use.

Figure 1:
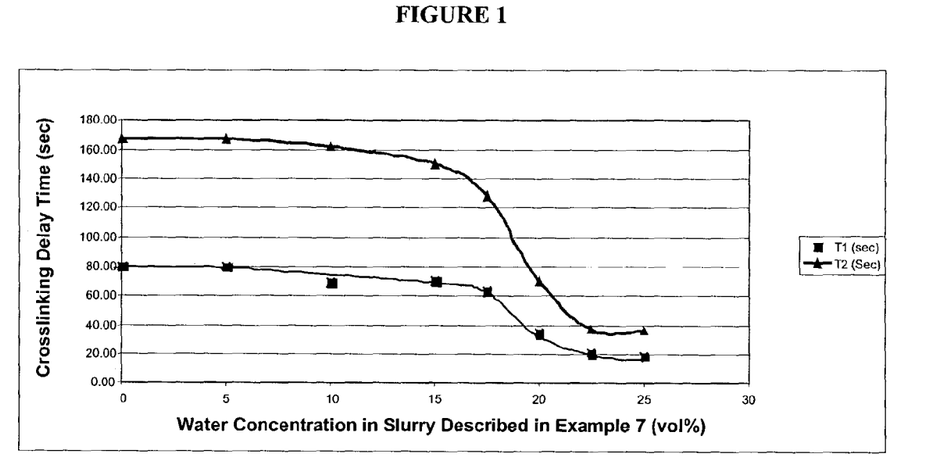
FIG. 1 is a graph which shows the effect of water addition on crosslinking rate of the borate crosslinker slurry prepared in accordance with Example 7. The crosslinking rate is expressed as vortex closure time $T_1$ and $T_2$.
Figure 2:
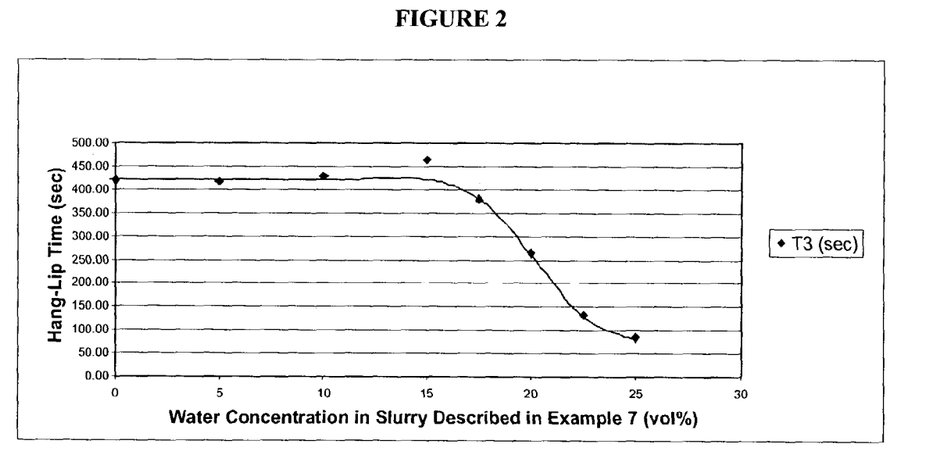
FIG. 2 is a graph which shows the effect of water addition on crosslinking rate of the borate crosslinker slurry prepared in accordance with Example 7. The crosslinking rate is expressed as hang lip time $T_3$.

Example 7 demonstrates the effect of water concentration in the boron crosslinker suspension system described in Example 1 on the crosslinking reaction rate of a water-soluble polymer solution. The crosslinking rates are shown in FIGS. 1 and 2. The data indicate that up to 15% (vol %) water can be added to the solution prepared according to Example 1 without affecting the crosslinking reaction rate. When the water concentration in the mixture is higher than about 15% (vol %), crosslinking delay times T1, T2 and T3 became shorter. This suggests that the addition of water accelerated the crosslinking rate of the solution prepared according to Example 1. None of those crosslinker suspensions with added water showed settling or precipitates, even after one month. Crosslinking rate tests were conducted within hours of their water dilution.

Comparative Example 8 demonstrates the effect of water concentration in the boron crosslinker suspension system described in Comparative Example 3 (a typical boron crosslinker suspension in current use) on the crosslinking reaction rate of a water-soluble polymer solution. Crosslinking tests could not be conducted, due to the rapid formation of precipitates, effectively making the crosslinker unusable. This Example clearly demonstrates the superiority of the boron crosslinker suspension of the claimed invention.

Example 9 demonstrates the effect of water concentration in the boron crosslinker suspension of the claimed invention on the crosslinking reaction rate of a water-soluble polymer solution where the temperature of the fluid is cooled from room temperature to 40° F. prior to addition of the boron crosslinker of the present invention. The results of this evaluation, shown in Table 2, demonstrate the superiority of the claimed boron crosslinker suspension in cold environs, whether this might be occasioned by cold field mix waters, or cold well bore temperatures, such as those encountered above the mud-line in offshore wells.

It is noted that the objects, aims and advantages of the claimed invention as set forth above are accomplished by the described invention. While the invention has been described in connection with specific embodiments, it is evident that many alternatives, modifications and variations thereof would be apparent to those skilled in the art after having been instructed by the foregoing description. Accordingly, it is intended to embrace all such alternatives, modifications and variations by the appended claims as set forth.

The invention claimed is:
1. A non-aqueous suspension comprising:
 (a) boron-containing particulates;
 (b) low molecular weight polyalkylene glycol; and
 (c) a suspension stabilizer comprising an hydrogenated castor oil or wax;

wherein the boron-containing particulates are selected from the group consisting of alkaline metal borates, boric acid, and mixtures thereof.

2. The suspension of claim 1 wherein boron-containing particulates comprise between about 0.1 weight percent to about 60 weight percent of the total suspension weight.

3. The suspension of claim 1 wherein said boron-containing particulates have an average particle size of about 0.1 microns to about 600 microns.

4. The suspension of claim 1 wherein said boron-containing particulates have an average particle size of about 1 micron to about 300 microns.

5. The suspension of claim 1 wherein said boron-containing particulates have an average particle size of about 5 microns to about 200 microns.

6. The suspension of claim 1 wherein the boron content (as percent B) of the non-aqueous suspension comprise between about 0.01 weight percent to about 45 weight percent of the total suspension weight.

7. The suspension of claim 1 wherein said low molecular weight polyalkylene glycol comprises between about 35 weight percent to about 99.8 weight percent of the total suspension weight.

8. The suspension of claim 1 wherein said low molecular weight polyalkylene glycol is selected from the group consisting of polyethylene glycol, polypropylene glycol, and mixtures thereof.

9. The suspension of claim 1 wherein said low molecular weight polyalkylene glycol has a molecular weight less than about 1000.

10. The suspension of claim 1 wherein said low molecular weight polyalkylene glycol has a molecular weight between about 100 and about 600.

11. The suspension of claim 1 wherein said low molecular weight polyalkylene glycol has a molecular weight between about 200 and about 500.

12. The suspension of claim 1 wherein the hydrogenated castor oil or wax comprises between about 0.1 weight percent to about 5.0 weight percent of the total suspension weight.

13. The suspension of claim 1 wherein the hydrogenated castor oil or wax comprises between about 0.3 weight percent to about 3.0 weight percent of the total suspension weight.

14. The suspension according to claim 1 wherein the amount of hydrogenated castor oil or wax comprises between about 0.5 weight percent to about 2.0 weight percent of the suspension.

15. The suspension of claim 1 further comprising one or more additives selected from the group consisting of salts, pH buffers, surfactants, emulsifiers, demulsifiers, foaming agents, antifoaming agents, water miscible co-solvents, preservatives, clay stabilizers, corrosion inhibitors, scale removers, paraffin solvents, iron chelants, hardness ion chelants, antioxidants, biocidal agents, gel preservatives and gel breakers.

16. A non-aqueous suspension comprising:
   (a) boron-containing particulates;
   (b) low molecular weight polyalkylene glycol;
   (c) a suspension stabilizer comprising an hydrogenated castor oil or wax; and
   (d) a thickener for the polyalkylene glycol;
wherein the boron-containing particulates are selected from the group consisting of alkaline metal borates, boric acid, and mixtures thereof.

17. The suspension of claim 16 wherein boron-containing particulates comprise between about 0.1 weight percent to about 60 weight percent of the total suspension weight.

18. The suspension of claim 16 wherein said boron-containing particulates have an average particle size of about 0.1 microns to about 600 microns.

19. The suspension of claim 16 wherein said boron-containing particulates have an average particle size of about 1 micron to about 300 microns.

20. The suspension of claim 16 wherein said boron-containing have an average particle size of about 5 microns to about 200 microns.

21. The suspension of claim 16 wherein said boron content (as percent B) of the non-aqueous suspension comprises between about 0.01 weight percent to about 20 weight percent.

22. The suspension of claim 16 wherein said low molecular polyalkylene glycol comprises between about 35 weight percent to about 99.8 weight percent of the total suspension weight.

23. The suspension of claim 16 wherein said low molecular polyalkylene glycol is selected from the group consisting of polyethylene glycol, polypropylene glycol, and mixtures thereof.

24. The suspension of claim 16 wherein said low molecular weight polyalkylene glycol has a molecular weight less than about 1000.

25. The suspension of claim 16 wherein said low molecular weight polyalkylene glycol has a molecular weight between about 100 and about 600.

26. The suspension of claim 16 wherein said low molecular weight polyalkylene glycol has a molecular weight between about 200 and about 500.

27. The suspension of claim 16 wherein the hydrogenated castor oil or wax stabilizer comprises between about 0.1 weight percent to about 5.0 weight percent of the total suspension weight.

28. The suspension of claim 16 wherein the hydrogenated castor oil or wax stabilizer comprises between about 0.3 weight percent to about 3.0 weight percent of the total suspension weight.

29. The suspension according to claim 16 wherein the amount of hydrogenated castor oil or wax comprises between about 0.5 weight percent to about 2.0 weight percent of the suspension.

30. The suspension of claim 16 wherein the polyalkylene glycol thickener is selected from the group consisting of partially neutralized polyacrylic acid, hydroxypropyl cellulose, highly substituted hydroxypropyl guar, hydrated thickening silica, and mixtures thereof.

31. The suspension of claim 16 further comprising one or more additives selected from the group consisting of salts, pH buffers, surfactants, emulsifiers, demulsifiers, foaming agents, antifoaming agents, water miscible co-solvents, clay stabilizers, preservatives, corrosion inhibitors, scale removers, paraffin solvents, iron chelants, hardness ion chelants, antioxidants, biocidal agents, gel preservatives and gel breakers.

32. A crosslinked hydraulic fracturing fluid comprising:
   (a) a water-soluble polymer; and
   (b) a non-aqueous boron crosslinker suspension comprising:
      (i) boron-containing particulates;
      (ii) a low molecular weight polyalkylene glycol, and
      (iii) a suspension stabilizer comprising a hydrogenated castor oil or wax;

wherein the polymer is crosslinked with the non-aqueous boron crosslinker.

33. The crosslinked fracturing fluid of claim 32 wherein the boron-containing particulates are selected from the group consisting of alkaline metal borates, boric acid, and mixtures thereof.

34. The crosslinked fracturing fluid of claim 32 wherein the amount of the boron-containing particulates is between about 0.1 weight percent and about 60 weight percent of the total suspension weight.

35. The crosslinked fracturing fluid of claim 32 wherein the amount of boron content (as percent B) of the non-aqueous suspension is between about 0.01 weight percent and about 20 weight percent of the total suspension weight.

36. The crosslinked fracturing fluid of claim 32 wherein the low molecular weight polyalkylene glycol is selected from the group consisting of polyethylene glycol, polypropylene glycol, and mixtures thereof.

37. The crosslinked fracturing fluid of claim 32 wherein the suspension stabilizer is a hydrogenated castor oil or wax.

38. The crosslinked fracturing fluid of claim 32 wherein the boron-containing particulates have an average particle size of about 0.1 microns to about 600 microns.

39. The crosslinked fracturing fluid of claim 32 wherein the amount of the low molecular weight polyalkylene glycol is between about 35 weight percent and about 99.8 weight percent of the total suspension weight.

40. The crosslinked fracturing fluid of claim 32 wherein the amount of suspension stabilizer is between about 0.1 weight percent to about 5 weight percent of the total suspension weight.

41. The crosslinked fracturing fluid of claim 32 wherein the water-soluble polymer contained in the water-soluble polymer solution is selected from the group of guar, hydroxyalkyl guar, carboxyalkyl guar, carboxyalkyl hydroxyalkyl guar, and mixtures thereof.

42. The crosslinked fracturing fluid of claim 32 wherein the amount of water-soluble polymer is between about 0.12 weight percent and 2.0 weight percent of total fracturing fluid weight.

43. The crosslinked fracturing fluid of claim 32 wherein the pH of the crosslinked fluid is greater than about pH 8.5.

44. A crosslinked hydraulic fracturing fluid comprising:
(a) a water-soluble polymer;
(b) a non-aqueous boron crosslinker suspension comprising:
(i) boron-containing particulates;
(ii) a low molecular weight polyalkylene glycol, and
(iii) a suspension stabilizer comprising a hydrogenated castor oil or wax; and
(c) water;
wherein the polymer is crosslinked with the non-aqueous boron crosslinker.

45. The crosslinked hydraulic fracturing fluid of claim 44 wherein the crosslinking reaction rate is accelerated by the addition of water.

46. The crosslinked hydraulic fracturing fluid of claim 45 wherein the amount of water is between about 10 weight percent and about 25 weight percent of the total weight of the crosslinker suspension.

47. The crosslinked hydraulic fracturing fluid of claim 45 wherein the fracturing fluid temperature is less than about 75° F. and wherein the amount of water is between about 10 weight percent and about 25 weight percent of the total weight of the crosslinker suspension.

48. A crosslinked hydraulic fracturing fluid comprising:
(a) a water-soluble polymer;
(b) a non-aqueous boron crosslinker suspension comprising:
(i) boron-containing particulates;
(ii) a low molecular weight polyalkylene glycol,
(iii) a suspension stabilizer comprising a hydrogenated castor oil or wax; and
(iv) a thickener for the polyalkylene glycol; and
(c) water;
wherein the polymer is crosslinked with the non-aqueous boron crosslinker.

49. A non-aqueous boron crosslinker suspension comprising:
(a) between about 30 weight percent and about 50 weight percent solid particles of an alkaline metal borate, boric acid, or mixtures thereof;
(b) between about 48 weight percent and about 70 weight percent low molecular weight polyethylene glycol; and
(c) between about 0.5 weight percent and about 2 weight percent hydrogenated castor wax.

50. The boron crosslinker suspension of claim 49 wherein the low molecular weight polyethylene glycol has an average molecular weight ranging from about 100 to about 500.

51. The boron crosslinker suspension of claim 49 wherein the low molecular weight polyethylene glycol has an average molecular weight of about 200.

52. A method of crosslinking one or more water soluble polymers comprising:
adding to a hydrated or colloidal dispersion of one or more water soluble polymers an effective crosslinking amount of a non-aqueous boron crosslinker comprising:
(a) boron-containing particulates;
(b) low molecular weight polyalkylene glycol; and
(c) a suspension stabilizer comprising an hydrogenated castor oil or wax.

53. The method of claim 52 wherein the water soluble polymers are selected from the group of polyvinyl alcohols, starches, derivatized starches, guar, derivatized guars, and locust bean gum.

54. The method of claim 53 wherein the derivatized guar is selected from the group of hydroxyalkyl guar, carboxyalkyl guar, carboxyalkyl hydroxyalkyl guar, and mixtures thereof.

55. A method of crosslinking one or more water soluble polymers comprising:
adding to a hydrated or colloidal dispersion of one or more water soluble polymers an effective crosslinking amount of a non-aqueous boron crosslinker comprising:
(a) boron-containing particulates;
(b) low molecular weight polyalkylene glycol;
(c) a suspension stabilizer comprising an hydrogenated castor oil or wax; and
(d) a thickener for the polyalkylene glycol.

56. The method of claim 55 wherein the water soluble polymers are selected from the group of polyvinyl alcohols, starches, derivatized starches, guar, derivatized guars, and locust bean gum.

57. The method of claim 56 wherein the derivatized guar is selected from the group of hydroxyalkyl guar, carboxyalkyl guar, carboxyalkyl hydroxyalkyl guar, and mixtures thereof.

58. The method of claim 55 wherein the thickener for the polyalkylene glycol is selected from the group consisting of partially neutralized polyacrylic acid, hydroxypropyl cellulose, highly substituted hydroxypropyl guar, fumed silica, hydrophobic silica, and mixtures thereof.

59. A method of fracturing a subterranean formation comprising:
(1) forming a hydraulic fracturing fluid comprising:
   (a) water
   (b) a water soluble polymer, and
   (c) a non-aqueous boron crosslinker suspension comprising:
      (i) boron-containing particulates;
      (ii) low molecular weight polyalkylene glycol; and
      (iii) a suspension stabilizer comprising an hydrogenated castor oil or wax, and
(2) pumping said fracturing fluid via tubing or casing into a subterranean formation with sufficient force to initiate a fracture.

60. A method of fracturing a subterranean formation comprising:
(1) forming a hydraulic fracturing fluid comprising:
   (a) water;
   (b) a water soluble polymer, and
   (c) a boron crosslinker suspension comprising:
      (i) boron-containing particulates;
      (ii) low molecular weight polyalkylene glycol;
      (iii) a suspension stabilizer comprising an hydrogenated castor oil or wax; and
      (iv) water; and
(2) pumping said fracturing fluid via tubing or casing into a subterranean formation with sufficient force to initiate a fracture.

61. A method of fracturing a subterranean formation comprising:
(1) forming a hydraulic fracturing fluid comprising:
   (a) water
   (b) a water soluble polymer, and
   (c) a boron crosslinker suspension comprising:
      (i) boron-containing particulates;
      (ii) low molecular weight polyalkylene glycol;
      (iii) a suspension stabilizer comprising an hydrogenated castor oil or wax;
      (iv) a thickener for the polyalkylene glycol; and
      (v) water; and
(2) pumping said fracturing fluid via tubing or casing into a subterranean formation with sufficient force to initiate a fracture.

62. The method of claim 59 wherein the fracturing fluid further comprises an alkaline compound sufficient to raise the pH of the fracturing fluid to about 8.5 or greater.

63. The method of claim 60 wherein the fracturing fluid further comprises an alkaline compound sufficient to raise the pH of the fracturing fluid to about 8.5 or greater.

64. The method of claim 61 wherein the fracturing fluid further comprises an alkaline compound sufficient to raise the pH of the fracturing fluid to about 8.5 or greater.

65. The non-aqueous suspension of claim 1 wherein the suspension has a PMCC flashpoint greater than about 140° F., has hexane extractable oil and grease of less than about 30 ppm, and has a boron content greater than about 1 weight percent.

66. The non-aqueous suspension of claim 16 wherein the suspension has a PMCC flashpoint greater than about 140° F., has hexane extractable oil and grease of less than about 30 ppm, and has a boron content greater than about 1 weight percent.

67. The boron crosslinker suspension of claim 49 wherein the suspension has a PMCC flashpoint greater than about 140° F., and has hexane extractable oil and grease of less than about 30 ppm.

68. The method of claim 52 wherein the boron crosslinker suspension has a PMCC flashpoint greater than about 140° F., has hexane extractable oil and grease of less than about 30 ppm, and has a boron content greater than about 1 weight percent.

69. The method of claim 55 wherein the boron crosslinker suspension has a PMCC flashpoint greater than about 140° F., has hexane extractable oil and grease of less than about 30 ppm, and has a boron content greater than about 1 weight percent.

70. The method of claim 54 wherein the hydroxyalkyl guar is hydroxypropyl guar, the carboxyalkyl guar is carboxymethyl guar, and carboxyalkyl hydroxyalkyl guar is carboxymethyl hydroxypropyl guar.

71. The method of claim 57 wherein the hydroxyalkyl guar is hydroxypropyl guar, the carboxyalkyl guar is carboxymethyl guar, and carboxyalkyl hydroxyalkyl guar is carboxymethyl hydroxypropyl guar.

* * * * *